Figure 1:
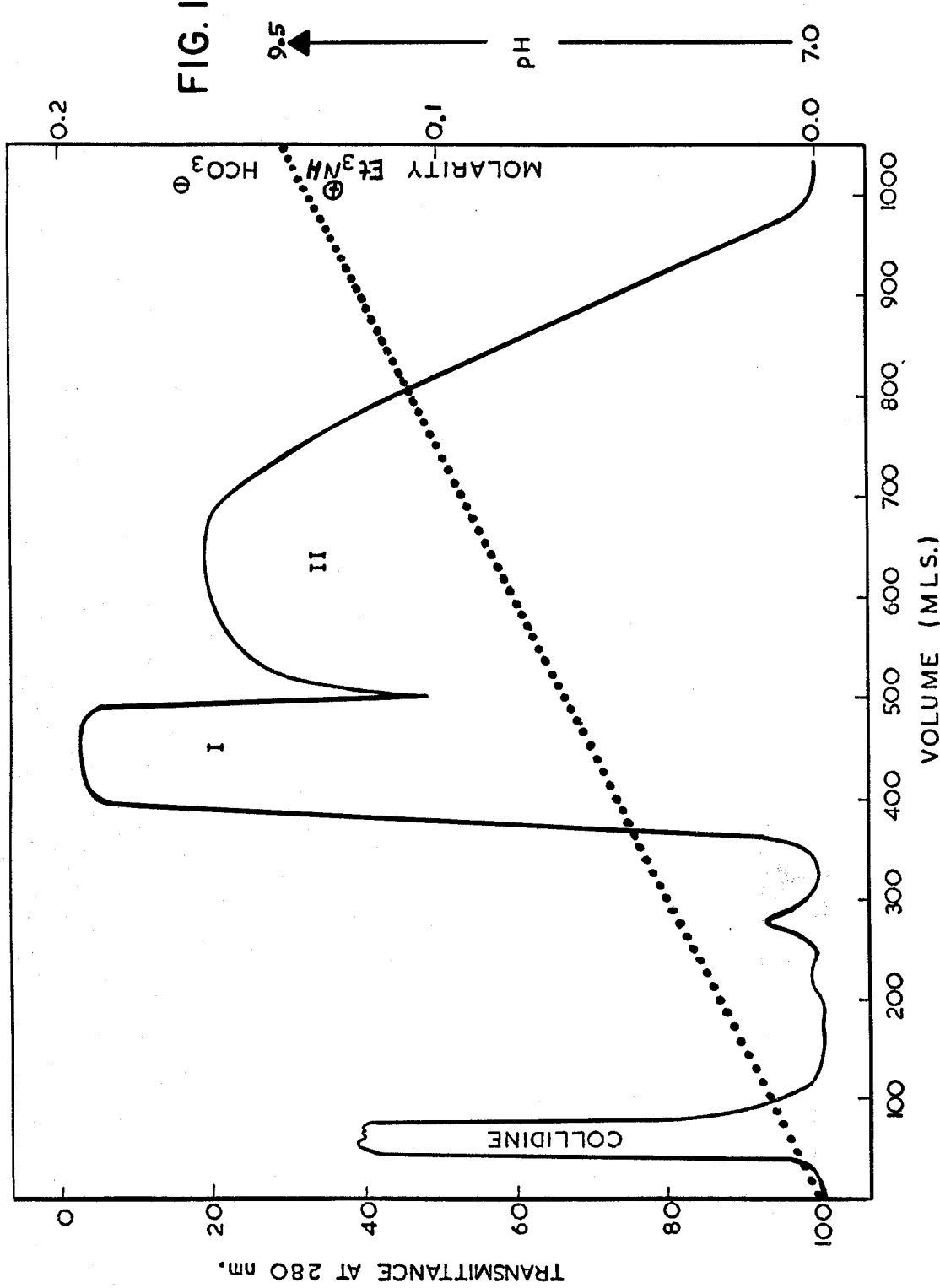

United States Patent [19]

Hutchinson et al.

[11] 3,935,185

[45] Jan. 27, 1976

[54] POLYNUCLEOTIDES OF POLY(5-HYDROXYCYTIDYLIC ACIDS)

[75] Inventors: David Wesley Hutchinson, Leamington Spa; Michael Anthony William Eaton, Aylesbury, both of England

[73] Assignee: G. D. Searle & Co., Chicago, Ill.

[22] Filed: Mar. 28, 1974

[21] Appl. No.: 455,877

[30] Foreign Application Priority Data
Apr. 2, 1973 United Kingdom............... 15671/73

[52] U.S. Cl... 260/211.5 R; 195/28 N; 424/180;181
[51] Int. Cl.²......................................... C07H 19/10
[58] Field of Search ............................ 260/211.5 R

[56] References Cited
UNITED STATES PATENTS

| | | | |
|---|---|---|---|
| 3,462,414 | 8/1969 | Wechter | 260/211.5 R |
| 3,652,538 | 3/1972 | Niblack | 260/211.5 R |

OTHER PUBLICATIONS

Eaton et al., "Biochimica et Biophysica Acta" Vol. 319, 1973, pp. 281–287.

*Primary Examiner*—Johnnie R. Brown
*Attorney, Agent, or Firm*—Elliot N. Schubert; John J. McDonnell

[57] ABSTRACT

Poly(5-hydroxycytidylic acids), produced by the enzymatic polymerization of 5-hydroxycytidylic acid, possess the ability to induce the production of interferon and, furthermore, exhibit anti-viral properties.

2 Claims, 1 Drawing Figure

POLYNUCLEOTIDES OF POLY(5-HYDROXYCYTIDYLIC ACIDS)

The present invention relates to novel polynucleotides, more particularly to poly(5-hydroxycytidylic acid), and to novel means for its synthesis.

The synthesis of polynucleotides has become important since they have been shown to be capable of interfering with virus growth in animal cells. However it has been difficult to obtain a polynucleotide which can be prepared in a satisfactory yield, which is active in virus interference and which is not toxic to a mammalian recipient.

The purpose of the present invention is to provide a novel polynucleotide which combines all these properties. There are also provided novel methods for the synthesis of such polynucleotides.

According to the present invention there is provided a polynucleotide comprising poly 5-hydroxycytidylic acid of lengths greater than ten residues of 5-hydroxycytidine. Those polynucleotides containing greater than ten but not more than 200 residues are particularly preferred. The starting material for the preparation of poly(5-hydroxycytidylic acid) is cytidine diphosphate as the trisodium salt. Conventionally, this is treated with bromine and pyridine, and then with an anion exchange resin. However this method affords a very low yield. It has now been found that treatment of cytidine diphosphate with bromine followed by 2,4,6-collidine results in a greatly improved yield of the 5-hydroxy derivative. It is further found that addition of an agent which catalyses dehydrobromination, in conjunction with the bromine, greatly enhances the yield of 5-hydroxycytidine diphosphate. For example, excess mercuric oxide or silver oxide may be added in suspension with the bromine.

Accordingly, the present invention provides a process for the production of poly(5-hydroxycytidylic acid) which comprises reacting together bromine, cytidine diphosphate and 2,4,6-collidine and subsequent polymerization of the 5-hydroxycytidine diphosphate obtained. The 5-hydroxycytidine diphosphate is prepared by the direct addition of bromine liquid to an aqueous solution of cytidine diphosphate trisodium salt at 0°. Excess bromine may be removed by extraction with a suitable solvent, for example, cyclohexene. Reaction of the aqueous residue with a base such as pyridine, although the preferred reagent is 2,4,6-collidine, leads to 5-hydroxycytidine diphosphate. The reaction is allowed to proceed for between 1 and 2 hours at 37°C.

The 5-bromo and 5-hydroxy derivatives of cytidine diphosphate may be separated by chromatography according to conventional techniques. In a preferred method, the derivatives are separated on a column of triethylaminoethyl cellulose. Conventionally, the pH of such a column eluant is about 7.0, but it has been found that a greatly improved separation may be achieved if the pH of the column eluant is about 9.5. The 5-bromocytidine diphosphate is eluted first and then the 5-hydroxycytidine diphosphate in a pure form, and the fractions containing the 5-hydroxycytidine diphosphate are collected and pooled.

The 5-hydroxycytidine diphosphate of the invention is polymerized by the action of polynucleotide phosphorylase, according to conventional principles. However, for the purpose of the present invention, the rate of polymerization is found to be dependent on the concentration of magnesium ions in the medium, and high concentrations are therefore preferred. Thus, equimolar concentrations of 5-hydroxycytidine diphosphate and magnesium ions are incubated in a trischloride buffer, in the presence of the enzyme.

The resulting polynucleotide is deproteinized, for example by treatment with a mixture of chloroform and isopentanol or other suitable solvent mixtures. The solution of polynucleotide is then dialyzed to remove salts in the solution and the final solution is lyophilized to provide hygroscopic poly(5-hydroxycytidylic acid).

The absence of residues other than 5-hydroxycytidine diphosphate in the polynucleotide may be established by various means. The polynucleotide may be degraded enzymatically and the residual monomer units may be separated and analyzed by chromatography. Additionally, the use of a pure preparation of 5-hydroxycytidine diphosphate in the polymerization to the polynucleotide ensures the preparation of the homopolymer poly(5-hydroxycytidylic) acid. It is the essence of the present invention that the polynucleotide should contain substantially only residues of 5-hydroxycytidine diphosphate and not consist of a heteropolymer containing other nucleotide residues.

The polynucleotides of the present invention consist of molecules of different molecular weights containing different numbers of nucleotide residues. It is not intended that the invention should be limited to polynucleotides of a particular molecular weight, and the term "polynucleotide" is understood to apply to all oligoand polynucleotides containing more than ten nucleotide residues. The molecular weight of the present polynucleotides will be different for different conditions of polymerization. For example, polymerization carried out using polynucleotide phosphorylase bound to an insoluble support, results in a polymer with an average molecular weight greater than that obtained using soluble enzyme. The approximate molecular weight may be estimated from the sedimentation rate of the polynucleotides by centrifugation in a salt gradient and it is found that a typical molecular weight for material polymerized using soluble enzyme is in the range of 40,000 to 80,000, and using insolubilized enzyme, is in the range of 100,000 to 150,000.

The polynucleotides according to the present invention possess the ability to induce the production of interferon and are further useful as anti-viral agents. The present compounds may therefore be used to prevent infection upon exposure to virus or to alleviate an established virus infection. For this purpose, the compound may be administered to a mammal, in any suitable carrier material, such as a buffered aqueous solution. The route of administration will depend upon the formulation used and an intravenous route is considered most effective for the delivery of the material to the mammal.

The preferred novel methods for the synthesis of the present compounds and the properties of these compounds are described in the following examples. However, these examples are not intended to limit or define in any way the scope of the invention.

EXAMPLE 1

Bromine is slowly added to a 10% W/V solution of cytidine diphosphate trisodium salt in water at 0°C. until a yellow color persists. The solution is then shaken with cyclohexene to remove excess bromine. 2, 4, 6-Collidine is then added and the emulsion incubated for 2 hours at 37°C. After cooling, the mixture is extracted 4 times with 2 parts of ether. The aqueous layer is applied to a triethylaminoethyl cellulose column, in the bicarbonate form, and is eluted with a linear gradient made by adding triethylammonium bicarbonate (0.14 M adjusted to pH 9.5 by the addition of triethylamine) to water (1 l.). 5-Bromocytidine diphosphate is eluted first, followed by 5-hydroxycytidine diphosphate at about 0.1 M bicarbonate, as shown in peak II in FIG. 1.

The fractions containing 5-hydroxycytidine diphosphate are pooled, evaporated to dryness and excess triethylammonium bicarbonate is removed by repeated addition and evaporation of methanol. The residue is converted by means of a Dowex 50 (sulfonated styrene-divinylbenzene polymer cation exchange resin, potassium form) column into the pale yellow, hygroscopic tripotassium 5-hydroxycytidine 5'-diphosphate.

The 5-hydroxycytidine diphosphate prepared as described above is polymerized by polynucleotide phosphorylase in a trischloride buffer (0.15 M. pH 9.0) containing 2.5 mM ethylenediamine tetraacetic acid and 0.02% sodium azide. 3000 Units phosphorylase per g. 5-hydroxycytidine diphosphate are required for a reasonable rate of reaction and equimolar concentration of substrate and magnesium ions are required.

The incubation medium is deproteinized by repeated extraction with chloroform/isoamyl alcohol (5:2, v/v) and the aqueous phase desalted by sequential dialysis against 0.2 M potassium chloride, 0.02 M potassium ethylenediamine tetraacetic acid (pH 8.0), 0.02 M potassium ethylenediamine tetraacetic acid (pH 7.0) and twice against water. The resulting solution is lyophilized at 0°C. to give a hygroscopic poly(5-hydroxycytidylic acid) in approximately 25% yield.

The poly(5-hydroxycytidylic acid) prepared above has an $S_{20,W}$ of 2.0–5.0 as determined by ultracentrifugation in an isokinetic sucrose gradient containing sodium acetate, at pH 7.0, indicating a molecular weight of 40,000–80,000. It showed a single peak when subjected to polyacrylamide gel electrophoresis. The ultraviolet maximum of poly(5-hydroxycytidylic acid) at 20°C. in 0.3 M NaCl, 0.01 M sodium cacodylate at pH 6.5 was 292 nm. and at pH 11.0 was 320 nm.

EXAMPLE 2

An important property of poly(5-hydroxycytidylic acid) according to the present invention is its inability to form hybrids with other polynucleotides. This property is illustrated by the following observations. (a) Upon mixing equimolar proportions of poly(5-hydroxycytidylic acid) with polyinosinic acid, polyguanylic acid or polyadenylic acid, in a NaCl/0.1 M sodium cacodylate mixture at pH 6.5 at 37°C. for 12 hours, the ultraviolet spectra were purely additive, showing only mixing but no hybridization of the polynucleotides. (b) Under the conditions above no Tm (abrupt change in ultraviolet absorption) could be recorded at temperatures between 5°C. and 95°C., indicating a complete failure of the polynucleotides to hybridize. (c) The rate of hydrolysis of polyinosinic acid in 0.1 M Tris-HCl, 0.3 M NaCl by T-ribonuclease at 20°C. was the same in the presence or absence of poly(5-hydroxycytidylic acid) indicating once again that there was no hybridization between the polynucleotides. (d) When an equimolar mixture of polyinosinic acid and poly(5-hydroxycytidylic acid) in 0.3 M NaCl–0.01 M sodium cacodylate was applied to a "Sephadex" G-200 (dextran polymer having water regain value of 20 g. water/g. polymer) column, only polyinosinic acid and poly(5-hydroxycytidylic acid) were eluted, there being no formation of a complex between them.

EXAMPLE 3

The antiviral activity of poly(5-hydroxycytidylic acid) is illustrated by its ability in protecting cells in tissue culture against infection with Sindbis virus (100 $\times TCD_{50}$). This dose of virus conventionally kills the cells within two days, but treatment of the cells for one hour with 0.03 μg./ml. poly(5-hydroxycytidylic acid), twelve hours before addition of virus, fully protects the cells against infection.

EXAMPLE 4

Poly(5-hydroxycytidylic acid) is active in protecting mice against infection with encephalomyocarditis virus (EMC) infection. Mice are injected intraperitoneally with $10^5$ plaque forming units (PFU) of EMC virus, either alone or in conjunction with 100 μg. poly(5-hydroxycytidylic acid) or other polynucleotides. The average survival time of the mice is shown below.

| Polynucleotide | Average Survival (Hours) |
| --- | --- |
| None | 84.4 |
| Polyadenylic acid | 94.4 |
| Polyuridylic acid | 98.6 |
| Poly(5-hydroxycytidylic acid) | 120.6 |

The other polynucleotides provided no significant protection against infection with EMC virus. In contrast, poly(5-hydroxycytidylic acid) provided a significant prolongation of the life of the animals.

EXAMPLE 5

Poly(5-hydroxycytidylic acid) is also shown to provide protection of mice against infection with Semliki Forest Virus (SFV). Five day suckling mice are injected with $32 \times LD_{50}$ dose of SFV (measured at 2 days) and, 2 hours prior to this injection, are also injected with doses of poly(5-hydroxycytidylic acid), poly I/poly C or no polynucleotide. The protection offered by these agents is expressed as the percentage of the animals surviving at 20 days after injection.

| Polynucleotide | Dose | % Survival |
| --- | --- | --- |
| None | — | 0% |
| Polyinosinic/polycytidylic acid | 100 μg | 50% |
| Poly(5-hydroxycytidylic acid) | 100 μg | 75% |
| Poly(5-hydroxycytidylic acid) | 20 μg | 67% |

Poly(5-hydroxycytidylic acid) is therefore shown to be more active than the conventional interferon inducer polyinosinic/polycytidylic acid in protecting mice against infection with SFV, even when the poly(5-hydroxycytidylic acid) is administered at a lower dose.

It is further shown that high doses of poly(5-hydroxycytidylic acid) administered alone to mice do not exhibit toxicity resulting in death. Thus doses of up to 400 mg polynucleotide per kilogram of mouse result in no deaths at 14 days. Clearly the present compounds exhibit strong antiviral activity at doses which have no acute toxicity to the animal.

What is claimed is:

1. Poly(5-hydroxycytidylic acids) containing greater than ten and up to 200 5-hydroxycytidine residues, inclusive.

2. A poly(5-hydroxycytidylic acid) according to claim 1, containing 100-200 5-hydroxycytidine residues and characterized by a sedimentation constant ($S_{20,W}$) of 2.0–5.0, a molecular weight of 40,000–80,000, a single peak when subjected to polyacrylamide gel electrophoresis and an ultraviolet maximum, measured at 20°C. in 0.3 M sodium chloride and 0.01 M sodium cacodylate, of 292 nm. at pH 6.5 and of 320 nm. at pH 11.0.

* * * * *